(12) United States Patent
Barron

(10) Patent No.: US 11,344,451 B2
(45) Date of Patent: May 31, 2022

(54) LIMITED DEPTH CORNEAL PUNCH

(71) Applicant: Mark B. Barron, Grand Blanc, MI (US)

(72) Inventor: Mark B. Barron, Grand Blanc, MI (US)

( * ) Notice: Subject to any disclaimer, the term of this patent is extended or adjusted under 35 U.S.C. 154(b) by 38 days.

(21) Appl. No.: 16/661,232

(22) Filed: Oct. 23, 2019

(65) Prior Publication Data

US 2020/0121505 A1 Apr. 23, 2020

Related U.S. Application Data

(60) Provisional application No. 62/749,366, filed on Oct. 23, 2018.

(51) Int. Cl.
*A61F 9/013* (2006.01)
*A61F 2/00* (2006.01)
*A61F 2/14* (2006.01)

(52) U.S. Cl.
CPC .......... *A61F 9/0133* (2013.01); *A61F 2/0095* (2013.01); *A61F 2/142* (2013.01)

(58) Field of Classification Search
CPC ...... A61F 9/007; A61F 9/00763; A61F 9/013; A61F 9/0133; A61F 2/0095; A61F 2/14; A61F 2/142; A61F 2250/0004; A61F 2250/009; A61B 17/32; A61B 17/32053
See application file for complete search history.

(56) References Cited

U.S. PATENT DOCUMENTS

| | | | | |
|---|---|---|---|---|
| 5,011,498 A | * | 4/1991 | Krumeich | A61F 9/013 606/166 |
| 5,464,417 A | * | 11/1995 | Eick | A61F 9/007 606/166 |
| 5,649,944 A | * | 7/1997 | Collins | A61F 9/013 606/166 |

* cited by examiner

*Primary Examiner* — Robert A Lynch
(74) *Attorney, Agent, or Firm* — The Weintraub Group, PLC

(57) ABSTRACT

A single-use adjustable depth trephine corneal punch device that allows a goal trephination depth of a donor cornea to be set and cut prior to a surgical procedure for cutting selected portions of an actual patient cornea. The corneal punch includes a punch block having a central well for receiving a donor cornea, a punch top mounted atop the punch block and having a central cylindrical opening coaxially aligned with the well, a punch blade mounted atop the punch top and through the opening cooperates with the top for combined limited rotation and limited axial movement from a reference or "start" point and into juxtaposed relation against the cornea and a limited axial downward movement during rotation to make a shallow cut in the cornea.

14 Claims, 3 Drawing Sheets

LIMITED DEPTH CORNEAL PUNCH

CROSS-REFERENCE TO RELATED APPLICATION

This Application is a Completion Application of U.S. Provisional Patent Application Ser. No. 62/749,366 for Limited Depth Corneal Punch, filed Oct. 23, 2018, the disclosure of which is hereby incorporated by reference in its entirety, including the drawing.

BACKGROUND OF THE INVENTION

1. Field of the Invention

The present invention pertains to a single-use adjustable depth trephine device that allows a goal trephination depth of a donor cornea to be set and cut prior to a surgical procedure for cutting selected portions of an actual patient cornea.

2. Description of the Prior Art

Corneal transplant trephine devices were introduced in the 1980's for the cutting of donor cornea tissue in cases of cornea transplants. Typically, the diseased patient cornea was replaced with the donor tissue using a procedure called penetrating keratoplasty. In this procedure a total cut was made in the patient cornea using a trephine, and the entirety of the patient's cornea inside the cylindrical cut is removed and replaced with donor tissue that is sutured in place.

An example of the donor punch used in penetrating keratoplasty is shown in FIG. 1. The instrument consists of a punch block 10, a blade 12 fixed in place in a nylon top piece 14 and pegs 16 used to accurately locate the blade relative to the block, which in the representation below uses a vacuum to hold the donor tissue in place. The surgeon places the donor tissue endothelium-side up into the block, and then presses the blade firmly through the entirety of the donor tissue, resulting in a circular button that is the total thickness of the cornea.

FIG. 2 shows a vacuum trephine 18 which is a companion instrument used to remove the patient's cornea. The trephine comprises a threaded body assembly 20 that is fixed onto the patient's eye using a vacuum, and a cylindrical blade 22 which is held in a top piece 24 (referred to as the spoke wheel). The spoke wheel and blade are in the upper right and the body assembly in the lower left. The surgeon rotates the spoke wheel, and the threads lower the blade a distance that depends on the threads per inch on the spoke wheel and the body. A typical implementation would use 100 threads-per-inch, giving a vertical movement of the blade of 0.010 inch for each full revolution of the spoke wheel.

In many cases requiring corneal transplants, the surface of the cornea is healthy and only the bottom of the cornea (the endothelium) is diseased. Rather than replace the entire cornea, which often leads to severe astigmatism because of the suturing required in the penetrating keratoplasty procedure, doctors are now replacing only the lower part of the cornea that includes the endothelium.

There are several approaches currently used to replace the endothelium, and most of them require using only a thin layer of donor tissue rather than the full thickness. Surgeons and eye clinics often harvest the thin layer by making a shallow cut in the donor tissue, sometimes by just tapping on the punch top so that it only penetrates a small amount rather than the full thickness of the cornea. However, using this "touch" method is inaccurate and requires a certain amount of skill in this medical art.

There is no known device that has a rotating blade in a punch top for use with harvesting donor tissue. However, in FIG. 3 there is shown an adjustable patient trephine from Moria that can be adjusted from 200 microns to 1200 microns. Moria also offers a punch that has a limited depth penetration, but the blade is fixed in position (such as a depth of 300 microns). The user cannot change the depth setting. Moria devices typically use a bent razor blade. The narrow range of angles produced by the Moria trephine is important because it indirectly affects the depth penetration and applications and is, therefore, not practical for use in harvesting donor tissue because it would require manual positioning in a separate punch block.

It is to be appreciated that there is a need for an efficient low-cost limited depth corneal punch apparatus and method of using, such as described herein. Accordingly, an object according to this invention is provision of a single-use adjustable depth trephine device that allows a goal trephination depth of the donor cornea to be set and cut prior to a surgical procedure for cutting selected portions of an actual patient cornea.

Another object hereof is a method and apparatus of replacing only the lower part of the cornea that includes the endothelium.

Another object of this invention is the provision of a limited depth corneal punch that enables the surgeon the ability to accurately penetrate a predetermined thickness of the cornea, rather that the full thickness of the cornea.

Another object of this invention is the provision of a corneal punch that effectively sets the depth penetration required in a given corneal operation.

SUMMARY OF THE INVENTION

According to this invention, there is provided a single-use adjustable depth trephine corneal punch device that allows a goal trephination depth of a donor cornea to be set and cut prior to a surgical procedure for cutting selected portions of an actual patient cornea, the corneal punch device comprising:
 (a) a punch block having a central well for receiving a donor cornea;
 (b) a punch top mounted atop the punch block and having a central cylindrical opening coaxially aligned with the well; and
 (c) means for cutting a selected portion of the donor cornea in the central well.

The means for cutting includes a punch blade mounted atop the punch top and through the opening for combined limited rotation less than about 312 degrees and limited axial movement from a reference or "start" point which can be greater than zero and into juxtaposed relation against the cornea and a limited axial downward movement during rotation to provide a shallow cut in the cornea.

Preferably, the means for cutting includes a reference cylinder mounted atop the punch top, and a cutting assembly including a cylindrical punch blade and a blade holder mounted in the reference cylinder for simultaneous rotation and axial movement through the opening.

The blade holder initially positions the cutting end of the blade atop the donor cornea.

Preferably, the means for cutting includes the blade holder. The blade holder includes a top and bottom surface and an arcuate groove in the bottom surface of less than about 312 degrees and having first and second ends, representing respectively, the "start" point and the final cut point of the blade, and a guide pin projecting up from the punch top and into the groove for limiting rotational and axial movement of the blade holder and associated blade, respectively.

Preferably the bottom end of the reference cylinder is formed with a radius of curvature to match the curvature of the well in the punch block and engage selected area of the cornea.

The present invention will be more clearly understood with reference to the accompanying drawings and to the following Detailed Description, in which like reference numerals refer to like parts and where:

DETAILED DESCRIPTION OF THE PREFERRED EMBODIMENT

Turning now to the drawings, and, in particular, FIGS. 4-7 illustrate a single-use adjustable depth trephine corneal punch device 30 that allows a goal trephination depth of a donor cornea to be set and cut prior to a surgical procedure for cutting selected portions of an actual patient cornea according to this invention.

Figure 1:
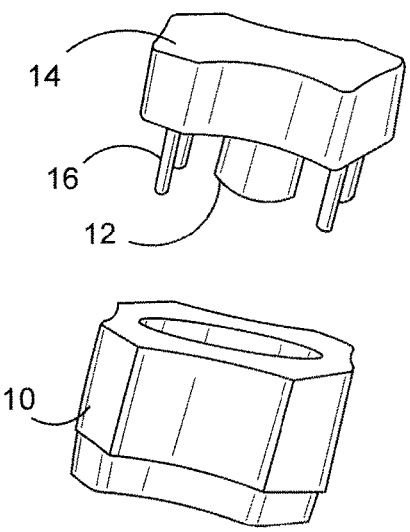
FIG. 1 is an assembly view of a prior art donor punch used in penetrating kerotoplasty.
Figure 2:
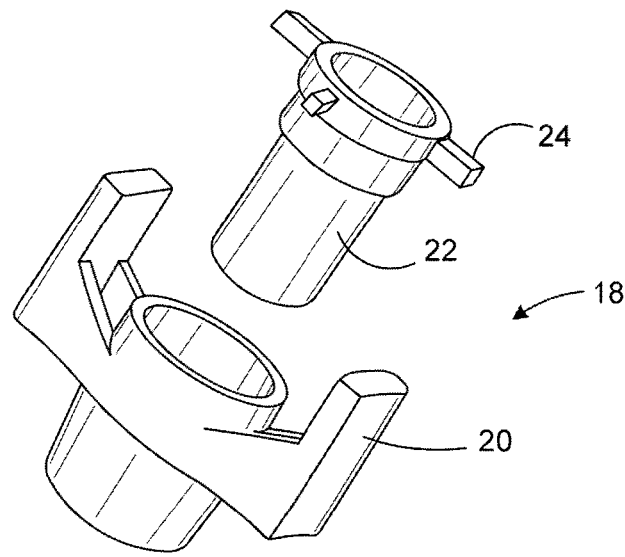
FIG. 2 is an assembly view of a Moria prior art limited depth corneal punch.
Figure 3:
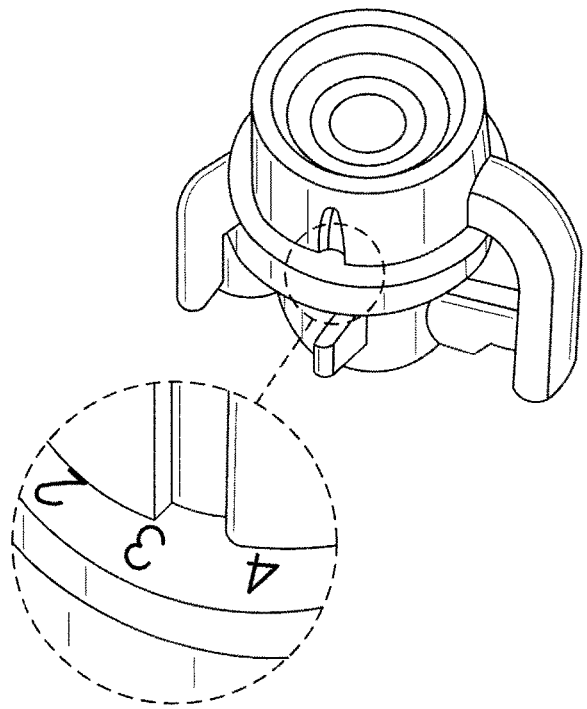
FIG. 3 is an assembly view of a prior art vacuum trephine showing a threaded body assembly that is fixed onto the patient's eye using a vacuum and a cylindrical blade held in a threaded top piece (a spoke wheel)
Figure 4:
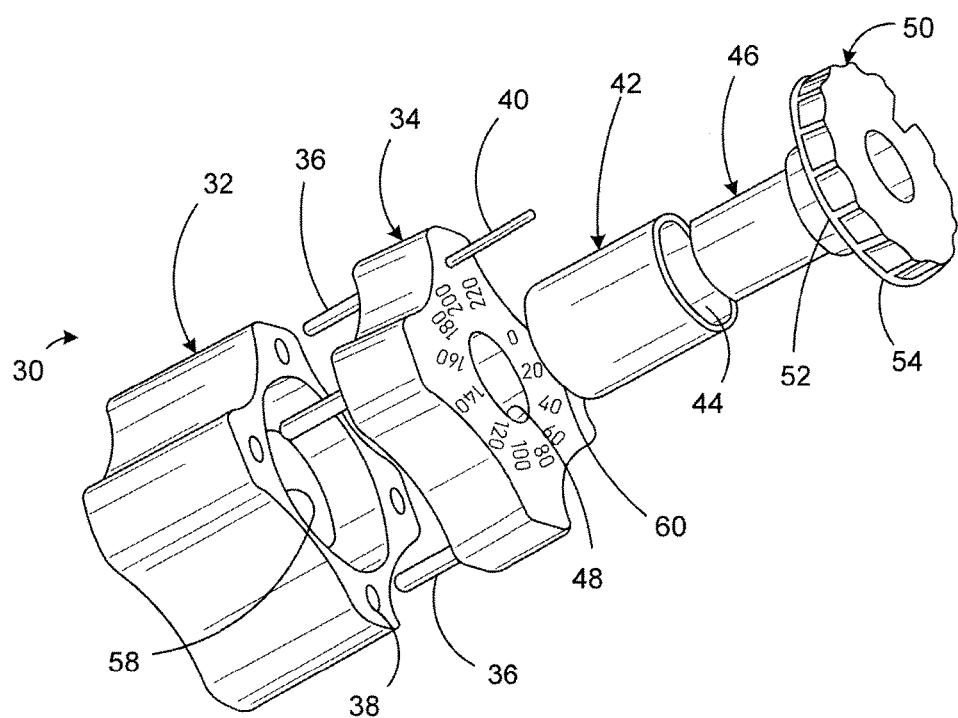
FIG. 4 is a cut-away elevation view of a punch blade threadably secured into a reference cylinder and below a rotator wheel thereof.

As shown in FIG. 4, the corneal punch 30 comprises, in part:
(a) a punch block 32, a punch top 34 with bottom pins 36 which register with receiving holes 38 in the punch block and an oppositely extending top guide pin 40;
(b) a reference cylinder 42 with internal threads 44 at the top end;
(c) a cylindrical punch blade 46; and
(d) a blade holder or wheel 50 for rotating the punch blade.

The blade holder 50 has external threads 52 for connection to the threads 44 of the reference cylinder 42 and bottom surface 54 formed with a defined groove 56 for receiving the guide pin.

The guide pin 40 and groove 56 limit rotation of the clockwise and/or counterclockwise rotation of the blade holder 50. A threaded connection predetermines the axial advance of the punch blade 46 from a "start" position to a desired corneal penetration to provide a limited depth cut.

The punch block 32 has a contoured central well or cavity 58 for receiving a donor cornea.

Preferably, the bottom end 60 of the reference cylinder 42 has a curvature to match the curvature of the well 58.

The punch top 34 includes a central opening 48 sized to pass the punch blade 46, the opening in juxtaposition with the well 58 of the punch block 32.

The reference cylinder 42 is attached to the top surface of the punch top 34. The blade holder 50 and punch blade 46 are held in place by an adhesive. The blade holder 50 is threadably secured to the reference cylinder 42.

When the instrument 30 is assembled, the punch blade 46 is lowered to a "start" position, which is the point at which the blade just touches the donor cornea, being prevented from penetrating further because the reference cylinder 42 stops the blade from penetrating the cornea.

As the blade holder is rotated, the punch blade is lowered below the reference cylinder by an amount that is determined by the threads on the blade holder and the cylindrical piece. In a preferred embodiment, there are 100 threads per inch, so a full rotation of the blade holder will only give a depth of 0.010 inches (254 micrometers).

The blade holder is designed such that it can rotate only a limited amount, thereby limiting the ultimate depth of penetration of the blade into the donor tissue.

The small guide pin 40 extending upward from the punch top 34 is beneath the blade holder 50 and nests within the groove 56 in the blade holder. The groove 56 extends between two end points on the circumference of the blade holder so that full counterclockwise rotation of the holder puts the blade at the "start" point. The maximum clockwise rotation in a preferred embodiment herein is about 312 degrees. This corresponds to a maximum depth of 220 micrometers using the 100 threads per inch. That amount may be increased or decreased using alternate threading protocols.

In one embodiment, the punch top 34 may be numbered to show incremental movements. Preferably, the top 34 will have a start point and numbered locations of 100, 150, and 200 micron increments. The blade holder 50 is cutout so that the corresponding number will show at these increments. Alternate threading schema would use different numbering.

Figure 5:
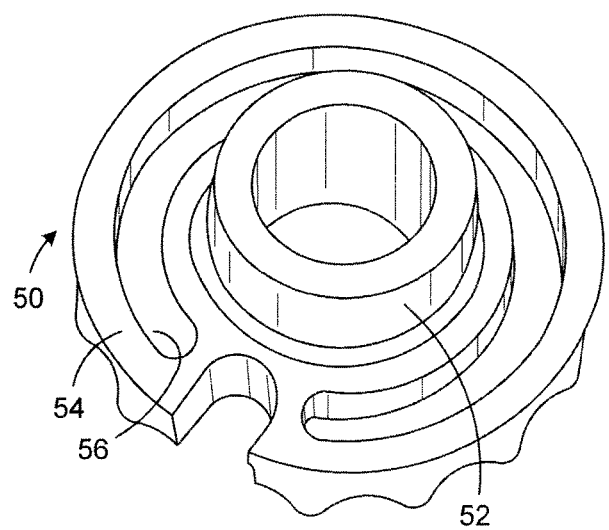
FIG. 5 is a perspective view of the bottom of the rotator wheel showing a rotation limiting groove formed therein.

FIG. 5 illustrates the bottom of the blade holder 50 and the groove 56 formed therein and a portion of the holder provided with the external threading 52.

Figure 6:
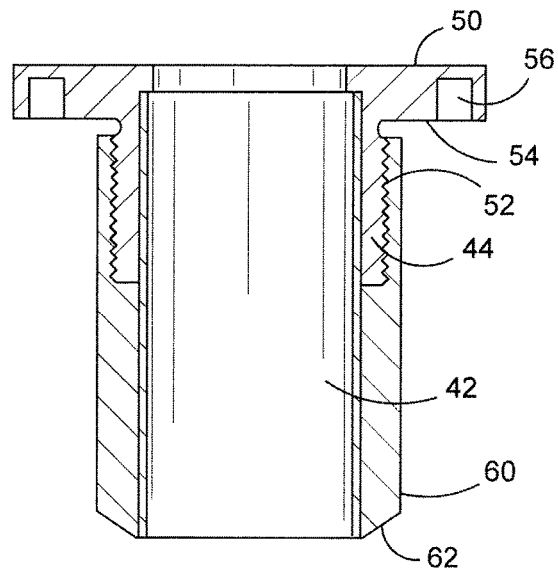
FIG. 6 is a plan view of the cutting blade.

FIG. 6 illustrates, in a vertical cutaway cross-section, the blade holder 50 threadably engaged with the threaded top end portion of the reference cylinder 42. As shown, the punch blade 46 is telescopically inter-fitted in the reference cylinder with the top end of the blade adhesively connected to the blade holder, and the lower end of the reference cylinder 42 provided with a predetermined radius of curvature that matches the surface of the well 58.

Figure 7:
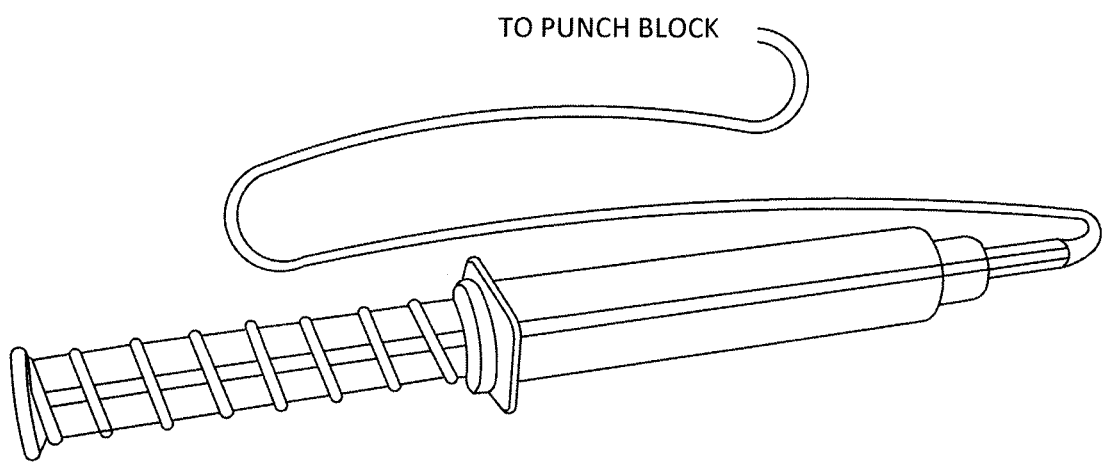
FIG. 7 is an assembly view of an optional vacuum which may be used in conjunction herewith.

In some applications, and as shown in FIG. 7 a vacuum may be employed with the punch block 32 to draw the donor cornea into contact with the well 58. A vacuum is applied using a syringe or containing a compression spring 102 attached to a plunger 104, such syringe is connected to the block using silicone tubing (not shown).

The foregoing description of specific embodiments of the present invention have been presented for purposes of illustration and description. They are not intended to be exhaustive or to limit the invention to the precise form disclosed, and modifications or variations are possible in the light of the above teaching.

REFERENCE NUMBERS IN DRAWINGS 10 punch block
12 blade
14 nylon top piece 16 pegs
18 companion instrument
20 threaded body assembly
22 top piece (spoke wheel)
24 upper peak/22
26 lower peak/22
30 limited depth corneal punch
32 punch block
34 punch top
36 pegs/34
38 receiving holes/32
40 guide pin/32
42 reference cylinder
44 internal threads/42
46 cylindrical punch blade
48 central opening/34
50 blade holder or wheel
52 external threads/50
54 bottom surface/52
56 defined groove/50
58 central well or cavity/32
60 bottom end/42
62 radius of curvature/42, w/58

Having thus described the invention, what is claimed is:

1. A single-use adjustable depth trephine corneal punch for cutting selected portions of a cornea, comprising:
   (a) a punch block having a central well for receiving a donor cornea;
   (b) a punch top mounted atop the punch block and having a central cylindrical opening coaxially aligned with the well;
   (c) means for cutting a selected portion of the donor cornea in the central well, the means for cutting includes a punch blade mounted atop the punch top and through the central cylindrical opening, the blade and the top cooperating for a combined limited rotation of the punch; and
   (d) wherein the top and blade combined for limited rotation of less than about 312° and limited axial movement from a start point and into juxtaposed relation against the cornea in a limited axial downward movement during rotation provides a shallow cut in the cornea.

2. The punch of claim 1 which further comprises a guide pin, and wherein the blade holder includes a top and bottom surface and an arcuate groove in the bottom surface of less than about 312°, the holder having first and second ends representing a start point and a final cut point of the punch blade.

3. The punch of claim 2 wherein the guide pin projects, is disposed on, and extends up from the punch top and into the arcuate groove for limiting rotational axial movement of the blade holder and punch blade.

4. The punch of claim 1 wherein the central cylinder opening is formed with a radius of curvature to match the radius of curvature of the well in the punch block to enable engagement with selective areas of the cornea.

5. The punch of claim 1 wherein:
   the means for cutting further includes a reference cylinder mounted atop the punch top and a cutting assembly including the punch blade and a blade holder mounted in the reference cylinder for simultaneous axial movement through the opening.

6. A single-use trephine corneal punch device for cutting selected portions of a cornea, comprising:
   (a) A punch block having receiving holes formed therein;
   (b) a punch top having bottom pins which register with the receiving holes in the punch block and an opposed extending top guide pin;
   (c) an internally threaded reference cylinder;
   (d) a cylindrical punch blade; and
   (e) an externally threaded blade holder for rotating the punch blade, and wherein the blade holder includes a top and bottom surface and an arcuate groove in the bottom surface of less than about 312°.

7. The device of claim 6 wherein the blade holder is externally threaded for connection to the internal threads of the reference cylinder, the blade holder further including a bottom surface having a groove for receiving the guide pin and wherein the top guide pin and groove cooperate to limit rotation of the clock-wise and/or counter clock-wise rotation of the blade holder.

8. A single-use adjustable depth trephine corneal punch for cutting selected portions of a cornea, comprising:
   (a) a punch block having a central well for receiving a donor cornea;
   (b) a punch top mounted atop the punch block and having a central cylindrical opening coaxially aligned with the well; and
   (c) means for cutting a selected portion of the donor cornea in the central well, the means for cutting includes a punch blade mounted atop the punch top and through the central cylindrical opening, the blade and the top cooperating for a combined limited rotation of the device is of less than about 312° and limited axial movement from a start point and into juxtaposed relation against the cornea in a limited axial downward movement during rotation to provide a shallow cut in the cornea.

9. The punch of claim 8 wherein:
   the means for cutting further includes a reference cylinder mounted atop the punch top and a cutting assembly including the punch blade and a blade holder mounted in the cylinder for simultaneous rotation and axial movement through the opening.

10. The punch of claim 9 wherein the blade holder includes (a) a top and bottom surface and an arcuate groove in the bottom surface of less than about 312°, the holder having first and second ends representing a start point and a final cut point of the blade and (b) a guide pin.

11. The punch of claim 10 wherein the guide pin projects, is disposed on, and extends up from the punch top and into the groove for limiting rotational axial movement of the blade holder and associated blade.

12. The punch of claim 11 wherein the reference cylinder is formed with a radius of curvature to match the curvature of the well in the punch block to enable engagement with selective areas of the cornea.

13. The punch of claim 8 wherein:
   (a) the punch block has at least one receiving hole;
   (b) an internally threaded reference cylinder;
   (c) a cylindrical punch blade; and
   (d) a blade holder for rotating the punch blade.

14. The punch of claim 13 wherein:
   the blade holder is externally threaded for connection to the internal threads of the reference cylinder, the blade holder further including a bottom surface having a groove for receiving the guide pin and wherein the guide pin and groove cooperate to limit rotation of the clock-wise and/or counter clock-wise rotation of the blade holder.

* * * * *